(12) United States Patent
Chochinov et al.

(10) Patent No.: US 8,288,366 B2
(45) Date of Patent: Oct. 16, 2012

(54) FORMULATION FOR HAIR GROWTH

(76) Inventors: Ronald H. Chochinov, Ventura, CA (US); Martha Gonzalez, Oxnard, CA (US)

( * ) Notice: Subject to any disclaimer, the term of this patent is extended or adjusted under 35 U.S.C. 154(b) by 1436 days.

(21) Appl. No.: 11/471,827

(22) Filed: Jun. 20, 2006

(65) Prior Publication Data

US 2007/0292538 A1 Dec. 20, 2007

(51) Int. Cl.
*A61K 31/56* (2006.01)

(52) U.S. Cl. .................. 514/169; 514/171

(58) Field of Classification Search .......... 514/169, 514/171
See application file for complete search history.

(56) References Cited

U.S. PATENT DOCUMENTS

| | | |
|---|---|---|
| 5,183,817 A | 2/1993 | Bazzano |
| 5,189,212 A | 2/1993 | Ruenitz |
| 5,514,672 A | 5/1996 | Bazzano |
| 5,527,772 A | 6/1996 | Holick |
| 5,629,002 A | 5/1997 | Weuffen et al. |
| 5,661,141 A | 8/1997 | Petrow |
| 5,725,851 A | 3/1998 | Wong et al. |
| 5,739,111 A | 4/1998 | Mahe |
| 5,840,690 A | 11/1998 | Holick |
| 5,843,422 A | 12/1998 | Wong et al. |
| 5,910,493 A | 6/1999 | Golbs et al. |
| 5,965,551 A | 10/1999 | Smart et al. |
| 5,972,962 A | 10/1999 | Belfield et al. |
| 5,980,875 A | 11/1999 | Mousa |
| 6,001,812 A | 12/1999 | Mahe |
| 6,017,893 A | 1/2000 | Segelman |
| 6,066,618 A | 5/2000 | Holick |
| 6,075,005 A | 6/2000 | Lurie |
| 6,171,604 B1 | 1/2001 | Mousa |
| 6,204,258 B1 | 3/2001 | Smart et al. |
| 6,464,111 B2 | 10/2002 | de LaForcade et al. |
| 6,555,532 B1 | 4/2003 | Smart et al. |
| 6,664,291 B2 | 12/2003 | Chiang et al. |
| 6,723,744 B2 | 4/2004 | Aspnes et al. |
| 6,838,484 B2 | 1/2005 | Steiner et al. |
| 6,924,310 B2 | 8/2005 | Chiang et al. |
| 6,939,846 B2 | 9/2005 | Lipton et al. |
| 2001/0051657 A1 | 12/2001 | Chiang et al. |
| 2001/0056068 A1 | 12/2001 | Chwalisz et al. |
| 2002/0027146 A1 | 3/2002 | De LaForcade et al. |
| 2003/0078289 A1 | 4/2003 | Aspnes et al. |
| 2003/0162757 A1 | 8/2003 | Smart et al. |
| 2003/0162761 A1 | 8/2003 | Steiner et al. |
| 2003/0225040 A1 | 12/2003 | Dalton et al. |
| 2003/0232792 A1 | 12/2003 | Dalton et al. |
| 2004/0013719 A1 | 1/2004 | Holick |
| 2004/0014975 A1 | 1/2004 | Dalton et al. |
| 2004/0022838 A1 | 2/2004 | Holick |
| 2004/0029913 A1 | 2/2004 | Dalton et al. |
| 2004/0067979 A1 | 4/2004 | Dalton et al. |
| 2004/0077694 A1 | 4/2004 | Chiang et al. |
| 2004/0087810 A1 | 5/2004 | Dalton et al. |
| 2004/0138244 A1 | 7/2004 | Dalton et al. |
| 2004/0147489 A1 | 7/2004 | Dalton et al. |
| 2004/0147550 A1 | 7/2004 | Dalton et al. |
| 2004/0167103 A1 | 8/2004 | Dalton et al. |
| 2004/0197928 A1 | 10/2004 | Dalton et al. |
| 2004/0260092 A1 | 12/2004 | Miller et al. |
| 2004/0260108 A1 | 12/2004 | Dalton et al. |
| 2004/0265916 A1 | 12/2004 | Dalton et al. |
| 2005/0033074 A1 | 2/2005 | Dalton et al. |
| 2005/0107374 A1 | 5/2005 | Elbaum et al. |
| 2005/0182072 A1 | 8/2005 | Cao et al. |
| 2005/0209221 A1 | 9/2005 | Nunes et al. |
| 2005/0209333 A1 | 9/2005 | Chiang et al. |
| 2006/0057075 A1* | 3/2006 | Arkin et al. ............. 424/47 |
| 2007/0231377 A1* | 10/2007 | Abou-Nemeh ............ 424/450 |

FOREIGN PATENT DOCUMENTS

| | | |
|---|---|---|
| EP | 0123528 | 10/1984 |
| EP | 0424954 | 5/1991 |
| GB | 888631 | 1/1962 |
| GB | 2127845 | 4/1984 |
| JP | 09100220 | 4/1997 |

OTHER PUBLICATIONS

"Notification of Transmittal of the International Search Report and the Written Opinion of the International Searching Authority," dated Nov. 22, 2007; Chochinov, Ronald H., PCT/US2007/013832.
"Applying Women's Rogaine." *Women's Rogaine*. Pfizer (2003) Apr. 25, 2006 <http://www.womensrogaine.com/style_awr.asp>.
"Healthy Hair." *Nature Made*. Apr. 27, 2006 <http://www.naturemade.com/wellnesstopics/wt_articles.asp?articleid=94>.
"How to Use Rogaine." *Men's Rogaine*. Pfizer (2005) Apr. 25, 2006 <http://www.rogaine.com/3_howtouse.asp>.
"Johnson's Baby Shampoo." *Johnson's Baby. . .* Apr. 27, 2006 <http://www.johnsonsbaby.com/products/shampoo/baby-shampoo>.
Kaufman, Keith D., et al., "Finasteride in the treatment of men with androgenetic alopecia," *J Am Acad Dermatol* (Oct. 1998); vol. 39, No. 4, Pt. 1, pp. 578-588.
Lucky, Anne W., et al, "A randomized, placebo-controlled trial of 5% and 2% topical minoxidil solutions in the treatment of female pattern hair loss," *J Am Acad Dermatol* (2004); vol. 50, pp. 541-553.
Margesson, J., "Thyroid Disease and the Skin," *Thyroid Foundation of Canada*. (2000) Apr. 27, 2006 <http://www.thyroid.ca/Articles/EngE9B/html>.
"Patient Information about Propecia." Brochure 9329304. Merck & Co., Inc. (Oct. 2004): 3 pp.
"Propecia." Brochure 9328505. Merck & Co., Inc. (Oct. 2004): 11 pp.

(Continued)

*Primary Examiner* — Renee Claytor
(74) *Attorney, Agent, or Firm* — Blakely Sokoloff Taylor & Zafman LLP (57) ABSTRACT

A composition and method for hair growth are described. The composition may include a dihydrotestosterone blocker and a thyroid source. Alternatively, the composition may include an estrogen source and a thyroid source. The composition may further include a base to facilitate application of the composition. A progestagen source, an antioxidant and/or a vitamin may further be added to the composition. The method may be a method of application comprising applying 0.5 ounces of a composition comprising a dihydrotestosterone blocker and a thyroid source to human skin, rubbing the composition into the skin, allowing the composition to remain on the skin for a period of between five minutes and ten minute and removing the composition.

21 Claims, 8 Drawing Sheets

OTHER PUBLICATIONS

Safer, Joshua D., "Thyroid Hormone and Hair Growth: Clinical and Basic Features," (2002), pp. 189-193.

"The Science Behind Progaine." *Progaine*. Apr. 25, 2006. <http://www.progaine.com/science.asp>.

Shimer, Elizabeth, "Hair Today, Gone Tomorrow?" Changes, pp. 95-102, Jan. 1, 2006.

"Super B Complex." *Nature Made*. Apr. 27, 2006 <http://www.naturemade.com/ProductDatabase/prd_prod.asp?productid=77>.

"What is Hormone Replacement Therapy (HRT)?" *University of Maryland Medical Center*. (2002) Apr. 25, 2006 <http://www.umm.edu/patiented/articles/what_hormone_replacement_therapy_hrt_000040_4.htm>.

"Women's Institute for Fine & Thinning Hair Sponsored by Rogaine." Brochure. *Rogaine*, pp. 3-22, Jan. 1, 2000.

* cited by examiner

FORMULATION FOR HAIR GROWTH

BACKGROUND

1. Field
Compositions and methods for hair growth.

2. Background

Androgenic alopecia is the most common form of scalp hair loss in both men and women. It has been estimated that more than 50 percent of men over 50 are affected by the condition and approximately 12 percent of men affected have lost most of their hair by the age of 30. According to the American Academy of Dermatology, by the age of 40, approximately 40 percent of women have begun to experience some hair loss.

Androgenic alopecia is caused by an androgen-dependent process which causes miniaturization of scalp hair follicles. Scalp dihydrotestosterone (DHT), a hair loss promoter formed from testosterone, is believed to be a major initiator of the process. Testosterone is converted into DHT by an enzyme known as 5-alpha reductase (5α-reductase). Men with androgenic alopecia typically exhibit lower levels of total testosterone, higher levels of unbound/free testosterone, and higher levels of total free androgens including DHT. Thus, it is believed that an increase in DHT levels contributes to hair loss.

In women, it has been recognized that when estradiol and progesterone levels are extremely high, such as during pregnancy, an increase in hair growth is experienced. During the postpartum period, however, when estradiol and progesterone levels decrease, hair loss is experienced. Thus, estradiol and progesterone levels are believed to be additional factors which may contribute to hair loss. Estradiol is a steroid derived from cholesterol. Synthesis of estradiol involves a key intermediary androstenedione, a steroid hormone, which is converted to testosterone which in turn undergoes aromatization to estradiol, or, alternatively, androstendione is aromatized to estrone which is converted to estradiol. Progesterone is a naturally occurring steroid hormone belonging to a class of hormones called progestagens and is synthesized from pregnenolone, a derivative of cholesterol.

Thyroid hormone may also play a role in hair loss. In particular, a common complaint of patients suffering from thyroid disease, and in particular hypothyroidism, is hair loss. Hypothyroidism is a disease characterized by insufficient production of thyroid hormone by the thyroid gland. Hormones produced by the thyroid include thyroxine ($T_4$) and triiodothyronine ($T_3$). These hormones regulate the rate of metabolism and affect the growth and rate of function of many other systems in the body. T3, in particular, has been shown in one study to stimulate hair growth in mice with a mutant hairless gene when applied topically. (Safer, Joshua D., Thyroid Hormone and Hair Growth: Clinical and Basic Features; 74th Annual Meeting of the American Thyroid Association, Meet the Professor Workshops, pages 187-193 (Oct. 10, 2002-Oct. 13, 2002)).

Current FDA approved treatments for alopecia condition in males and females include drug based treatments. In particular, FDA approved treatments for males include five percent minoxidil (ROGAINE®) and finasteride (PROPECIA®) administered systemically. For women, topical two percent minoxidil (ROGAINE®) has been approved. Other treatments considered have included herbal extracts.

For the most part, however, the above described treatments, particularly ROGAINE® and PROPECIA®, merely maintain existing hair while having little effect on hair regrowth. In addition, PROPECIA® is not safe for use by women and children and must be prescribed by a physician. Moreover, topical treatments, such as topical applications of minoxidil involve several steps which must be performed in addition to the user's daily hair care regimen twice a day.

BRIEF DESCRIPTION OF THE DRAWINGS

The following illustration is by way of example and not by way of limitation in the figures of the accompanying drawings in which like references indicate like elements. It should be noted that references to "an" or "one" embodiment in this disclosure are not necessarily to the same embodiment, and such references mean at least one.

DETAILED DESCRIPTION

The methods and compositions described herein provide for a safe and effective treatment for androgenic alopecia in both men and women. In particular, a hormone-enriched treatment composition is described that may be applied topically with minimal steps involved. In one aspect, the composition may include a combination of a dihydrotestosterone blocker and a thyroid source. Still further the composition may include a progestagen source, and/or an antioxidant and/or vitamins. Each of these components may be included in the composition in an amount found safe and effective for treating androgenic alopecia. A base may further be included in the composition to facilitate topical delivery of the composition to a desired treatment site.

The components, including those which may optionally be added, of the composition, as well as methods for making and applying the composition, are described. Also, methods for assessing the safety and efficacy of the composition are described in detail.

Components

Components of the composition for treatment for androgenic alopecia in both men and women are described in detail below. Each of the components may be included in the composition in an amount found to be effective for topically treating androgenic alopecia without causing significant systemic hormonal abnormalities. In particular, it is recognized that substances applied to an epidermal skin layer may be absorbed through the skin layers and in some cases into a blood stream of the user. Absorption of a significant amount of a hormone may alter the natural hormonal balance of the user and is therefore undesirable. As will be described in reference to the figures and tables that follow, a composition formulation is described herein wherein no measurable hormone absorption from, for example, the scalp to the body occurs.

1. Dihydrotestosterone Blocker

High levels of DHT are typically associated with androgenic alopecia. Accordingly, it is believed that a component having a property to block DHT levels would be beneficial in treating androgenic alopecia. In this aspect, the term "dihydrotestosterone blocker" or "DHT blocker" as used herein refers to any component capable of locally inhibiting DHT production, including, but not limited to, components which decrease the levels of available 5α-reductase prior to testosterone binding with the enzyme or rely upon any other mechanism to reduce levels of DHT within the body.

A. Estrogen Source

In one embodiment, a dihydrotestosterone blocker may be an estrogen source. Estrogens are present in both men and women however are usually present at higher levels in women of reproductive age. There are three major naturally occurring estrogens in women, namely estradiol, estriol and estrone. In the body some of these are produced from androgens through enzyme action. Estradiol is produced from testosterone and estrone from androstenedione. Estradiol is mainly secreted from the ovaries. It has been recognized that estrogens may block testosterone thereby lowering DHT levels. Representatively, an estrogen source may include, but is not limited to, estrogen, estradiol, estradiol-17-beta, estradiol valerate, conjugated equine estrogens, piperazine estrone sulphate, estrone, estriol, estriol succinate and polyestriol phosphate, and synthetic estrogens such as ethinyl estradiol, quinestranol and mestranol.

The estrogen source may be included in the composition in an amount found to be effective for topically treating androgenic alopecia without causing significant systemic hormonal abnormalities. Representatively, in one embodiment, the composition may include at least 100 milligrams (mg) of the estrogen source. In other embodiments, the composition may include between 10 mg and 200 mg of the estrogen source, and in some embodiments between 50 mg and 150 mg.

B. Saw Palmetto

In one embodiment, an alternative or additional dihydrotestosterone blocker may be saw palmetto (Seranoa repens). Saw palmetto is an herb derived from berries of the saw palm tree. Saw palmetto has been found to inhibit 5-alpha-reductase thereby interfering with DHT binding to the androgen receptor. In one embodiment, the composition may include any amount and form of saw palmetto found to be effective for topically treating androgenic alopecia without causing significant systemic hormonal abnormalities. Representatively, the composition may include between 40 mg and 100 mg of saw palmetto, and in some embodiments between 160 mg and 240 mg.

2. Thyroid Source

In one embodiment, the composition may include a thyroid source. The thyroid source may be any thyroid related compound, natural or synthetic, having a property capable of treating androgenic alopecia. In one embodiment, the thyroid source may include, any tyrosine-based hormones produced by the thyroid gland, including, but not limited to, thyroxine ($T_4$) and triiodothyronine ($T_3$). In other embodiments, the thyroid source may be a synthetic thyroid hormone including, but not limited to, dessicated porcine thyroid, levothyroxine, liothyronine and/or liotrix. The thyroid source may be included in the composition in an amount found to be effective for topically treating androgenic alopecia without causing significant systemic hormonal abnormalities. Representatively, in one embodiment, the composition may include at least 100 micrograms (μg) of the thyroid source. In other embodiments, the composition may include between five μg and 200μg of the thyroid source and in some embodiments between 50 μg and 150 μg of the thyroid source.

3. Progestagen Source

In one embodiment, a composition may include a progestagen source. A progestagen source may include any hormone within the class of progestagen hormones including natural progesterone and synthetic progestins. Synthetic progestins may be derived from testosterone (C19 progestagens) or progesterone (C21 progestagens). Representative progestins may include, but are not limited to, C21 progestagens such as cyproterone acetate, dydrogesterone, medroxyprogesterone acetate, chlormadinone acetate, megestrol, drospirenone and promegestone and/or C19 progestagens such as norethisterone, (levo)norgestrel, lynestrenol, desogestrel, norgestimate, gestodene and tibolone. The progestagen source may be included in the composition in an amount found to be effective for topically treating androgenic alopecia without causing significant systemic hormonal abnormalities. Representatively, in one embodiment, the composition may include at least 100 mg of the progestagen source. In other embodiments, the composition may include between five mg and 200 mg of the progestagen source and in some embodiments, between 50 mg and 150 mg of the progestagen source.

4. Vitamins

In some embodiments, the composition may include one or more vitamins. Any vitamin having a property, for example, to nourish the hair, inhibit hair loss and/or enhance hair growth may be used. Representatively, suitable vitamins may include, but are not limited to, essential B vitamins such as thiamine, riboflavin, niacin, vitamin B6, folic acid, vitamin B12, biotin and pantothenic acid. The concentration of the vitamin in the composition should be sufficient to provide the desired benefit of treating alopecia. Such concentration can vary with the vitamin selected, the effect desired and the type and concentration of other components, and other like factors. Representatively, the composition may include between one mg and 200 mg of a vitamin(s), and in some embodiments between 50 mg and 250 mg of the vitamin(s).

5. Antioxidant

In some embodiments, the composition may include an antioxidant. Any antioxidant having a property, for example, to nourish the hair, inhibit hair loss and/or enhance hair growth may be used. Representatively, suitable antioxidants may include, but are not limited to, vitamin A, vitamin C, vitamin E, Coenzyme Q10, selenium, zinc as well as carotenoid terpentoids, bioflavonoids, alpha lipoic acid and phenolic acids and their esters. The concentration of the antioxidant in the composition should be sufficient to provide the desired benefit of treating alopecia. Such concentration can vary with the antioxidant selected, the effect desired and the type and concentration of other components, and other like factors. Representatively, the composition may include between 1 mg and 300 mg of the antioxidant, and in some embodiments between 2 mg and 100 mg.

6. Base

The above components of DHT blocker(s) (e.g. estrogen source(s), saw palmetto), thyroid source(s), and optional progestagen source(s), vitamin(s) and/or antioxidant(s) may be combined into a solution as a unit form that, in one embodiment, may be combined with an inert base.

The composition may be in any form suitable for topical application. In this aspect, the composition may include a base capable of being combined with the dihydrotestosterone blocker, estrogen source, thyroid source, progestagen source, antioxidant and/or vitamin to facilitate delivery of the composition to the skin of the user. In one embodiment, the base may be in the form of a cream, lotion, gel, oil or liquid. In other embodiments, the base may be in the form of a shampoo, conditioner, spray or niousse. In one embodiment, the base may be any commercially available product suitable for topical application to a region of the user's skin such as the scalp and/or hair.

For example, in some embodiments the base may be a shampoo. In this aspect, the base may include a cleansing surfactant such as, but not limited to, an anionic surfactant, a cationic surfactant, a nonionic surfactant and an amphoteric surfactant. Representative anionic surfactants may include, but are not limited to, sodium dodecyl sulfate (SDS), ammonium lauryl sulfate, and other alkyl sulfate salts, sodium laureth sulfate a.k.a. sodium dodecyl sulfate, alkyl benzene sulfonate, soaps, or fatty acid salts. Representative cationic surfactants may include, but are not limited to, cetyl trimethylammonium bromide (CTAB) a.k.a. hexadecyl trimethyl ammonium bromide, and other alkyltrimethylammonium salts, cetyl pyridinium chloride, polyethoxylated tallow amine (POEA), benzalkonium chloride. Representative nonionic surfactants may include, but are not limited to, alkyl poly(ethylene oxide) alkyl polyglucosides, such as octyl glucoside and decyl maltoside, fatty alcohols, cetyl alcohol, oleyl alcohol, cocamide MEA, cocamide DEA, and cocamide TEA. Representative amphoteric surfactants may include, but are not limited to, dodecyl betaine, dodecyl dimethylamine oxide, cocamidopropyl betaine and coco ampho glycinate. The concentration of the surfactant in the composition should be sufficient to provide the desired surface tension and viscosity to the composition, and as will be apparent to one of ordinary skill in the art.

The base may further include a conditioning agent to prevent drying of the skin and hair. Representative conditioning agents may include, but are not limited to, glycerin, propylene glycol, alpha hydroxyl acids, urea, lactic acid, oils, lanolin and silicone and its derivatives. Such conditioning agents should be physically and chemically compatible with the essential components of the composition, and should not otherwise unduly impair product stability, aesthetics or performance. The concentration of the conditioning agent in the composition should be sufficient to provide the desired conditioning benefits, as will be apparent to one of ordinary skill in the art. The concentration may vary with the conditioning agent, the conditioning performance desired, the average size of the conditioning agent particles, the type and concentration of other components, and other like factors.

Still further, the base may be any commercially available hair or skin care product, such as a baby shampoo including, but are not limited to, those sold under the brand names JOHNSON'S®, GERBER® and HUGGIES®. In other embodiments, any commercially available hair or skin care product, including but not limited to, those sold under the brand names DOVE®, SUAVE® and NEUTROGENA® may be used as the base.

Representatively, in one embodiment, the composition may include 100 mg of estradiol (estrogen source), 100 µg of triiodothyronine (thyroid source) and 100 mg of a liquid progesterone (progestagen source) combined with a base including water, cocamidopropyl betaine, PEG-80 sorbitan laurate, sodium trideceth sulfate, PEG-150 distearate, fragrance, polyquaternium-10, tetrasodium EDTA, quaternium-15, citric acid, yellow 10 and orange 4 at a total composition volume of 15 ounces. In one embodiment, a solution of the unit form (estradiol, triiodothyonine, progesterone) is added to and is mixed with the base.

In still further embodiments, the base may include a component capable of encapsulating the dihydrotestosterone blocker, estrogen source, thyroid source, progestagen source, antioxidant and/or vitamin. In this aspect, a liposome may be included in the base. Liposomes are small, spherical vesicles which consist of amphiphilic lipids, enclosing an aqueous core. The lipids are predominantly phospholipids which form bilayers similar to those found in biomembranes. Depending on the processing conditions and the chemical composition, liposomes may be formed with one or several concentric bilayers. Liposomes are often distinguished according to their number of lamellae and size. For example, a liposome may be a small unilamellar vesicle ("SUV"), a large unilamellar vesicle ("LUV"), a large multilamellar vesicle ("MLC") or a multivesicular vesicle ("MVV"). LUVs, MLVs and MVVs range in size from a few hundred nanometers to several microns. Representatively, the thickness of the membrane (phospholipids bilayer) measures approximately five to six nanometers. Liposomes tend to permeate skin layers at a faster rate than other compounds. Thus it is believed that when active ingredients are encapsulated by the liposomes they will be transported through, for example, the scalp at a faster rate than in an un-encapsulated form. Due to the thickness of the scalp tissue, although the liposome facilitates permeation of the components through the scalp, it will not permeate so far as to be systemically absorbed by the body.

Various techniques may be used to form the treatment agent/lipsome solution. Representatively, in one embodiment a mixture including 200 µg of triiodothyronine and 200 mg of estradiol may be added to a eight ounce liposome solution. The combination may be dissolved in water in the presence of a single-tailed surfactant. The dissolution process may be performed at temperatures ranging from about 40 degrees Celsius (° C.) to about 80° C., depending on the type of phospholipids, the surfactant, and the presence of other ingredients such as actives, antioxidants and preservatives. The resulting clear solution may then be slowly diluted at this temperature with an amount of twice-distilled water to yield a lamellar liquid crystalline phase. Upon addition of additional twice-distilled water, the system was converted to a vesicle dispersion.

Figure 8:
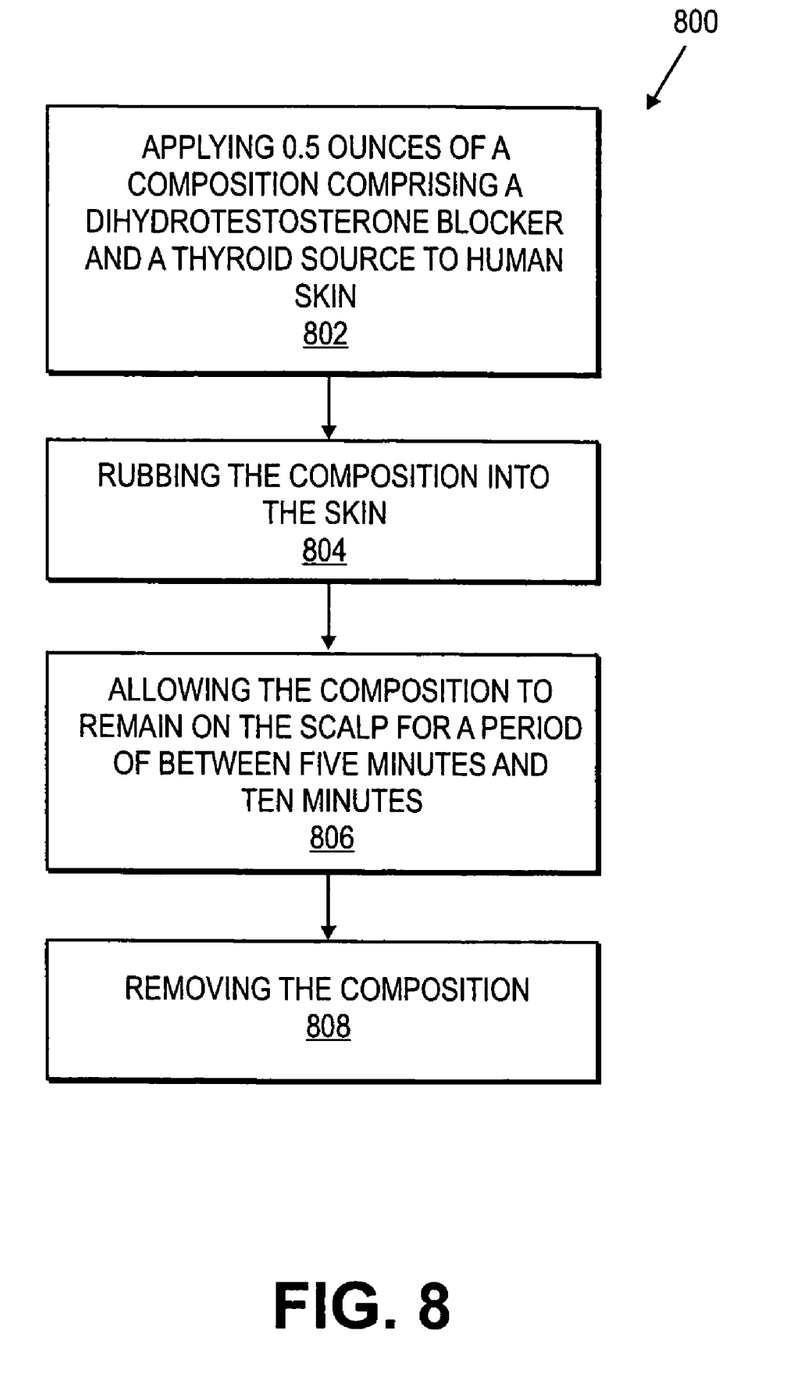
FIG. 8 is a flow chart of one embodiment of a method for application.

FIG. 8 illustrates a flow chart of a method of application. In one aspect, the composition is in the form of a shampoo and may therefore be substituted and used in place of the user's normal shampoo. In this aspect, the composition may be applied to a wet scalp during a user's daily shower routine. In other embodiments, the composition may be in a form suitable for application to skin regions of the user's body where the user desires hair growth. For example, in one embodiment the composition may be in the form of a lotion or cream and applied to an eye region to promote eyelash and/or eyebrow growth.

In one aspect, the composition may include a dihydrotestosterone blocker and a thyroid source. In other embodiments, the composition may include any one of, or a combination of, a dihydrolestoserone source, a thyroid source, a progestagen source, a vitamin and/or an antioxidant such as those previously described. In some embodiments, any amount of the composition found to be effective in treating androgenic alopecia may be applied to the scalp. Representatively, the composition includes 10-200 mg of an estrogen source(s) (e.g., estradiol), 5-200 µg of a thyroid source(s) (e.g., triiodothyrine), 5-200 mg of a progestagen source(s) (e.g., 100 mg of progesterone) in a base of 15 ounces of shampoo. Method 800 includes applying 0.25 ounces to one ounce (e.g. 0.5 ounces) of a composition to a human skin (block 802).

For example, in some embodiments, between 0.25 ounces and one ounce of the composition may be applied to the skin at once. Method 800 further includes rubbing the composition into the skin (block 804). Rubbing may be accomplished by using, for example, the user's finger or any other object or device found suitable for rubbing the composition into the user's scalp.

The composition may be allowed to remain on the skin for a period of between five minutes and ten minutes (block 806). It is believed that a period of between five minutes and ten minutes allows sufficient time for the composition to work its way into the skin and effectively treat symptoms of androgenic alopecia. In some embodiments, the composition may be allowed to remain on the skin for less than ten minutes.

The composition may be removed from the skin (block 808) after the above steps have been completed. Removal may be accomplished, by for example, rinsing off the skin with water or another fluid suitable for flushing the composition off of the skin. Since the desired effects of the composition on androgenic alopecia are experienced within between five minutes and approximately ten minutes of application, the user is free to continue with their normal skin routine once the composition is rinsed from the skin. Thus, where the composition is applied to the scalp, a conditioner or any other hair product, such as a styling product, may be applied to the scalp once the composition is removed. The above described method of application 800 may be used once a day over a period of approximately four months to six months. It is further contemplated that method 800 may be followed once a day for a period less than four months or greater than six months depending upon the individual results and goals of the user.

Analytical Methods

The composition for treating androgenic alopecia, when applied to the skin in a manner consistent with the methods of use described herein, provides for an effective treatment of androgenic alopecia with minimal systemic absorption or side effects in both men and women.

The following specific examples are set forth to illustrate analytical methods and data showing that when the composition is formulated and applied according to the method described herein effective treatment of androgenic alopecia is accomplished with minimal systemic absorption.

1. Experimental Procedure

A. Preparation of the Composition

In one embodiment, an active composition was prepared by adding 100 mg of estradiol, 100 μg of triiodothyronine and 100 mg of liquid progesterone to 15 ounces of a commercially available baby shampoo. Representative baby shampoos may include, but are not limited to, those sold under the brand names JOHNSON'S®, GERBER® and HUGGIES®. A placebo composition was further provided which included the shampoo without the hormonal component.

B. Study Participants

Both men and women were selected to participate in the experimental trials. In particular, 45 men and women, ages 22 years to 78 years, including established patients (RHC) and other persons were selected and placed into experimental groups. Ten women were assigned to a placebo group (Group A) and nine women were assigned to an active group (Group B). This was done by random assortment (NOS 1-19). An additional active group of 26 people, 17 men and nine women, were selected to take part in an open label trial to help expand the database (Group C). Persons with a history of breast cancer or open scalp lesions were excluded from the trial.

Those conducting the experiment were blinded as to which shampoo included the hormonal component. Only a pharmacist who formulated the shampoo was aware of which formulations were placebos and which were active.

C. Procedure

Each participant was given a 15 ounce bottle of baby shampoo in which hormones were or were not added to it. A variety of shampoo brands were used. Each participant was further given a one ounce plastic cup and asked to use a half ounce of shampoo daily. The shampoo was rubbed into the hair and scalp and then allowed to interact with the scalp for ten minutes. Participants were then instructed to rinse off the shampoo. Participants were allowed to use conditioner if desired. Each participant was scheduled to return every 30 days for a total of 180 days (e.g., 7 visits: 0, 30, 60, 90, 120, 150, 180 days). At each visit a picture of the scalp was taken. Blood was further drawn at each visit to test for levels of thyroid stimulating hormone (TSH), total thyroxine (T4), estradiol, progesterone, sex hormone binding globulin (SHBG) and, in men, serum testosterone levels. All assays were run on the IMMULITE® 2000 (Diagnostics Product Corporation, Los angeles, Calif.) using DPC test kits. Laboratory technologists did not know which participants were using active or placebo shampoos.

D. Results

Extensive lab data as illustrated in the figures and tables as follows showed no significant absorption of the added hormones in all groups at the different time periods both within and between groups. All data is given by actual numbers (Tables 1-7) or by comparison of average plus standard error measurement (SEM) (FIGS. 1-7). It should be noted that the range for hormone levels was at the low end and all changes in levels appear greater than they are due to the scale of the graphs.

Results of each group were assessed for absorption of the hormone and efficacy of the composition in treating androgenic alopecia. Absorption was determined by analyzing total T4, TSH and total testosterone levels as well as levels of estradiol, progesterone and sex hormone binding globulin and triiodothyronine resin uptake (T3RU) found in the blood of the study participants. Were significant absorption to occur, total T4, TSH and total testosterone levels would be expected to decrease, an increase in estradiol and progesterone levels would be expected and SHBG and T3RU would be expected to remain level. Absorption of T3 would be expected to cause reciprocal suppression of TSH which would have led to decreased total T4 levels. Efficacy was assessed by visual inspection of each participant's scalp and hair volume at each visit.

Results from visual inspection of each patient showed no hair growth in patients in Group A, the placebo group. Results from the remaining groups showed a distinct increase in hair from day 0 to days 150-180. In particular, in Group A, zero to 10 percent of the bald areas were covered at the end of the 180 day period. In Groups B and C, 65% to 98% of the bald areas were covered.

Figure 1:
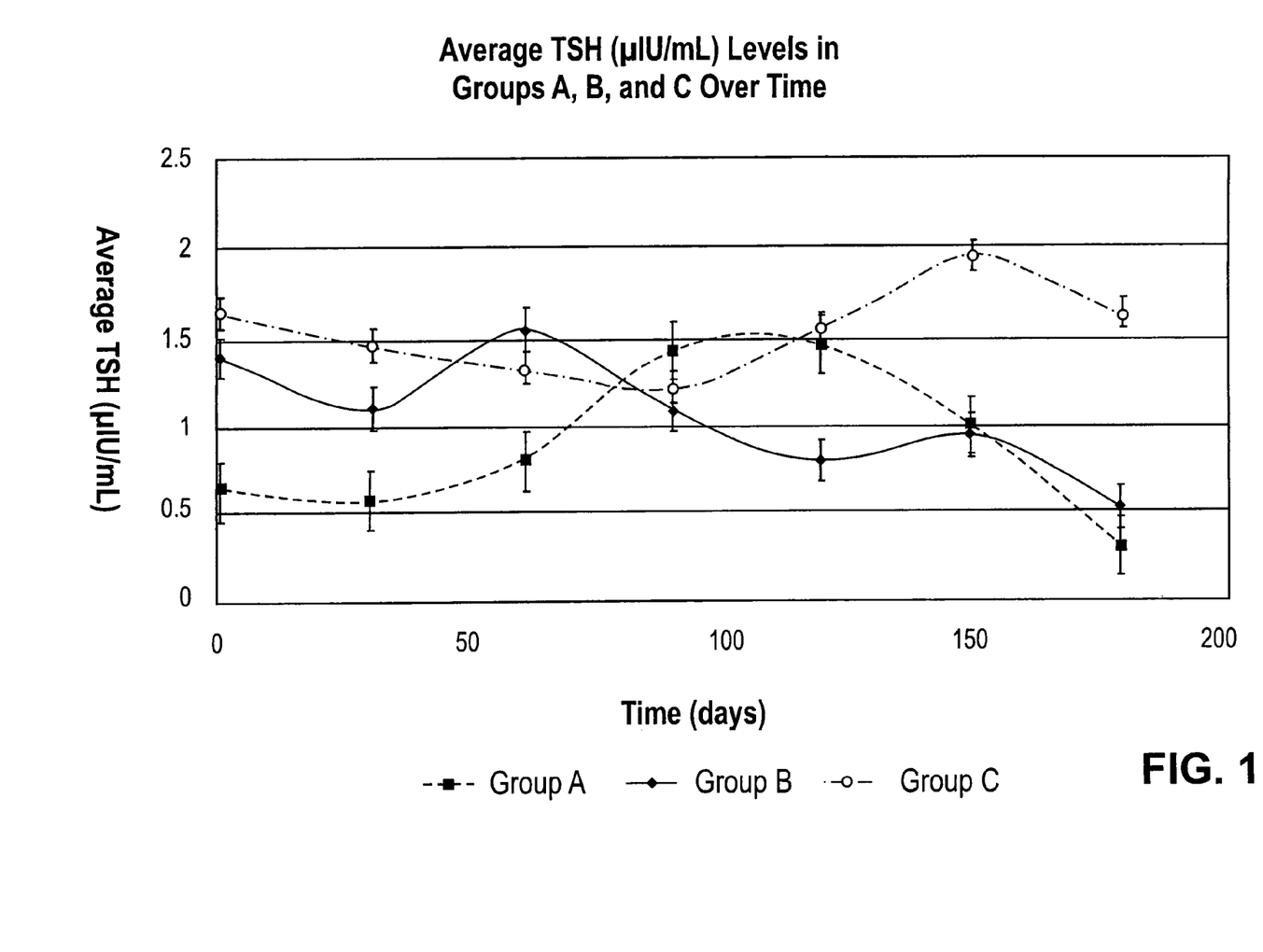
FIG. 1 illustrates TSH levels for patients in Groups A, B and C over a period of 180 days.

FIG. 1 and Table 1 illustrate TSH levels for patients in Groups A, B and C over a period of 180 days. As can be seen from FIG. 1 and Table 1, patients in Groups B and C did not experience a significant decrease in TSH levels over the 180 day period as would be expected if significant absorption of hormone had occurred.

TABLE 1

TSH (μIU/mL) Levels in Groups A, B and C

| Group | Subject | 0 | 30 | 60 | 90 | 120 | 150 | 180 |
|---|---|---|---|---|---|---|---|---|
| A | 1 |  | 0.25 | 1 | 3.5 | 1.6 |  |  |
|  | 2 | 0.71 | 2.1 | 1.1 | 1.7 | 1.2 | 1.2 | 0.4 |
|  | 3 | 0.41 | 0.4 |  | 0.7 |  |  | 0.3 |
|  | 4 | 1.9 |  | 1.8 | 1.2 | 2.8 | 1.8 |  |
|  | 5 | 0.3 |  |  |  |  |  |  |
|  | 6 | 0.3 |  |  |  |  |  |  |
|  | 7 | 0.01 | 0.01 | 0.03 |  |  | 0.07 |  |
|  | 8 | 0.63 |  |  |  |  |  |  |
|  | 9 | 0.05 | 0.02 | 0.06 | 0.1 | 0.31 |  |  |
|  | 10 | 1.16 | *1.74 |  |  |  |  |  |
| B | 1 | 0.07 | 0.09 | 0.14 | 0.18 | 0.16 | 0.48 | 0.59 |
|  | 2 | 0.63 | 0.7 | 0.7 | 0.9 | 0.6 | 0.6 | 0.49 |
|  | 3 | 2.4 | 2.4 | 2.6 | 2.6 |  | 3.0 |  |
|  | 4 |  | 1.0 | 1.5 | 0.99 | 1.95 | 0.5 |  |
|  | 5 | 0.4 | 0.1 | 0.1 | 1.14 | 0.5 | 0.4 |  |
|  | 6 | 3.3 |  | 4.5 |  |  |  |  |
|  | 7 | 0.7 | 1.05 | 0.6 | 0.7 |  | 0.8 | 0.6 |
|  | 8 |  |  |  |  |  |  |  |
|  | 9 | 2.2 | 2.3 | 2.2 |  |  |  |  |
| C | 1 |  | 1.0 | 1.2 |  |  |  |  |
|  | 2 | 3.4 | 5.4 | 4.9 |  | 2.8 | 3.9 | 3.2 |
|  | 3 | 3.0 |  |  |  |  |  |  |
|  | 4 | 1.2 | 1.0 | 1.4 |  | 1.2 | 1.6 | 1.0 |
|  | 5 | 0.54 |  | 0.5 | 1.0 |  |  |  |
|  | 6 | 0.61 | 0.7 | 0.7 | 1.1 |  |  |  |
|  | 7 | 1.15 |  |  |  |  |  |  |
|  | 8 |  | 1.4 | 1.2 | 0.9 |  |  |  |
|  | 9 | 0.83 | 1.0 |  | 1.0 | 1.2 |  |  |
|  | 10 | 1.42 | 1.4 | 1.5 | 1.7 | 1.4 | 1.2 | 1.2 |
|  | 11 | 1.9 | 1 | 1.4 | 1.3 | 1.4 | 2.4 | 2.5 |
|  | 12 |  | 1 | 1.2 | 0.9 | 1.6 | 2.4 |  |
|  | 13 |  | 1 | 1.2 | 1.1 | 1.7 | 1.6 |  |
|  | 14 |  | 3.4 |  | 4.2 | 3.1 | 2.4 |  |
|  | 15 |  |  |  |  |  |  |  |
|  | 16 | 3.8 |  |  |  |  |  |  |
|  | 17 | 0.43 |  |  |  |  |  |  |
|  | 18 | 0.68 | 0.8 | 0.6 | 0.7 | 1.2 |  |  |
|  | 19 | 0.12 | 0.12 | 0.11 | 0.05 | 0.6 | 0.2 | 0.4 |
|  | 20 |  | 1.3 | 1.6 | 1.1 | 2 | 1.8 |  |
|  | 21 | 1.6 |  |  |  |  |  |  |
|  | 22 | 3 |  |  |  |  |  |  |
|  | 23 | 2.2 |  |  |  |  |  |  |
|  | 24 |  | 0.9 | 1.1 | 0.9 | 0.7 |  |  |
|  | 25 |  | 1.8 |  |  |  |  |  |
|  | 26 | 1.9 |  |  |  |  |  |  |

Figure 2:
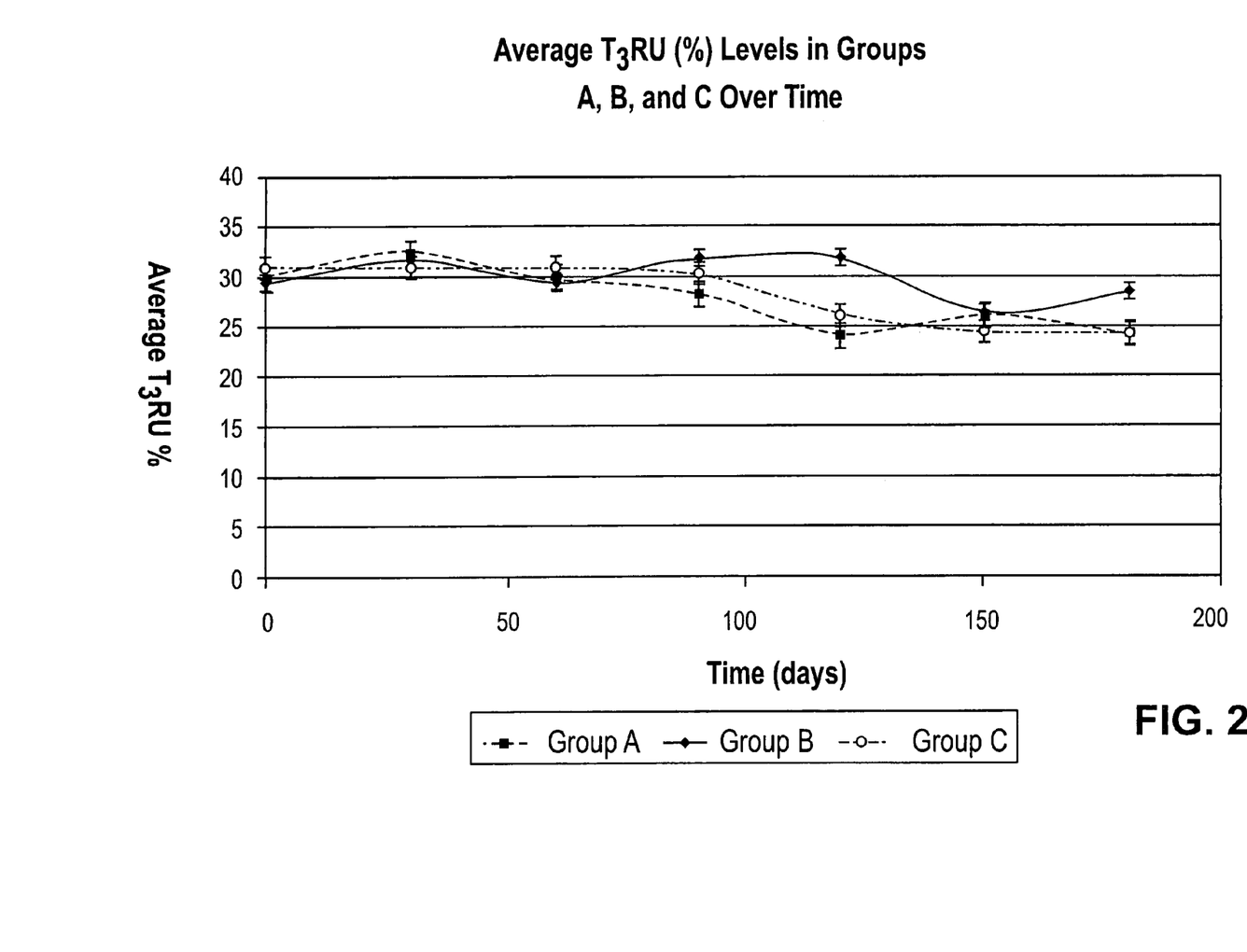
FIG. 2 illustrates T3RU levels for patients in Groups A, B and C over a period of 180 days.

FIG. 2 and Table 2 illustrate T3RU levels for patients in Groups A, B and C over a period of 180 days. As can be seen from FIG. 2 and Table 2, T3RU levels for patients in Groups B and C experienced a slight non-significant decrease over the 180 day period.

TABLE 2

T3RU (%) Levels in Groups A, B and C

| Group | Subject | 0 | 30 | 60 | 90 | 120 | 150 | 180 |
|---|---|---|---|---|---|---|---|---|
| A | 1 |  | 30.2 | 28.7 | 28.9 | 24.8 |  |  |
|  | 2 | 29.4 | 29.6 | 29.3 | 28.6 | 24.8 | 23.6 | 24.2 |
|  | 3 | 29.2 | 29.2 | 31.1 |  |  |  | 23.2 |
|  | 4 | 26.9 |  | 27.5 | 31 | 25.1 | 26.1 |  |
|  | 5 | 29.6 |  |  |  |  |  |  |
|  | 6 | 33 |  |  |  |  |  |  |
|  | 7 | 34.8 | 37.2 | 37.9 |  |  | 28.5 |  |
|  | 8 | 30.3 |  |  |  |  |  |  |
|  | 9 | 33.4 | 35.1 | 24.5 | 24.8 | 22.2 |  |  |
|  | 10 | 25.9 | 22.2* |  |  |  |  |  |
| B | 1 | 33.9 | 34.3 | 36 | 35.1 | 36.1 | 27.7 | 27.5 |
|  | 2 | 33.2 | 34.3 | 33.9 | 33.8 | 34.8 | 29.1 | 30.2 |
|  | 3 | 25.7 | 25.7 | 27.4 | 28.7 |  | 21.2 |  |
|  | 4 |  | 33.7 | 33.1 | 33.4 | 25.7 | 31.4 |  |
|  | 5 | 30.4 | 32.5 | 32.3 | 32.1 | 30.9 | 24.5 |  |
|  | 6 | 23.9 |  | 24.8 |  |  |  |  |
|  | 7 | 23.9 | 27.8 | 24.8 | 28.2 |  | 23.9 | 27.6 |
|  | 8 | 32.7 |  |  |  |  |  |  |
|  | 9 | 31.6 | 32.7 | 23.6 |  |  |  |  |
| C | 1 |  | 32.6 | 32.9 |  |  |  |  |
|  | 2 | 28.4 | 25.7 | 27.5 |  | 27.3 | 20.8 | 25.2 |
|  | 3 | 20.2 |  |  |  |  |  |  |
|  | 4 | 37.1 | 35.6 | 34.5 |  | 22.3 | 24.8 | 29.1 |
|  | 5 | 26.6 |  | 23.1 | 20.2 |  |  |  |
|  | 6 | 34.2 | 35.2 | 31.7 | 32.9 |  |  |  |
|  | 7 | 28.33 |  |  |  |  |  |  |
|  | 8 |  | 26.5 | 28.2 | 29.4 |  |  |  |
|  | 9 | 28.2 | 27.5 |  | 29.9 | 22.6 |  |  |
|  | 10 | 29.7 | 29.7 | 30.6 | 37 | 24.7 | 27.4 | 27.4 |
|  | 11 | 32.2 | 31.2 | 31.6 | 31.6 | 31.5 | 24.3 | 26.6 |
|  | 12 |  | 37.6 | 35 | 33.6 | 33.2 | 25 |  |
|  | 13 |  | 30.8 | 28.9 | 28.6 | 24.1 | 25.4 |  |
|  | 14 |  | 33.6 |  | 32.1 | 25.9 | 26.8 |  |
|  | 15 |  |  |  |  |  |  |  |
|  | 16 | 30.9 |  |  |  |  |  |  |
|  | 17 | 30.7 |  |  |  |  |  |  |
|  | 18 | 30.3 | 31.4 | 31 | 31.6 | 23.7 |  |  |
|  | 19 | 40 | 29.3 | 29 | 31.7 | 26.9 | 24.3 | 19.2 |
|  | 20 |  | 27.2 | 32.2 | 29.5 | 23.1 | 24.1 |  |
|  | 21 | 33.5 |  |  |  | 28.8 | 21.3 | 18.9 |
|  | 22 | 33.3 |  |  |  |  |  |  |
|  | 23 | 32.9 |  |  |  |  |  |  |
|  | 24 |  | 31.4 | 34.8 | 25.8 | 24 |  |  |
|  | 25 |  | 30.5 |  |  |  |  |  |
|  | 26 | 29 |  |  |  |  |  |  |

Figure 3:
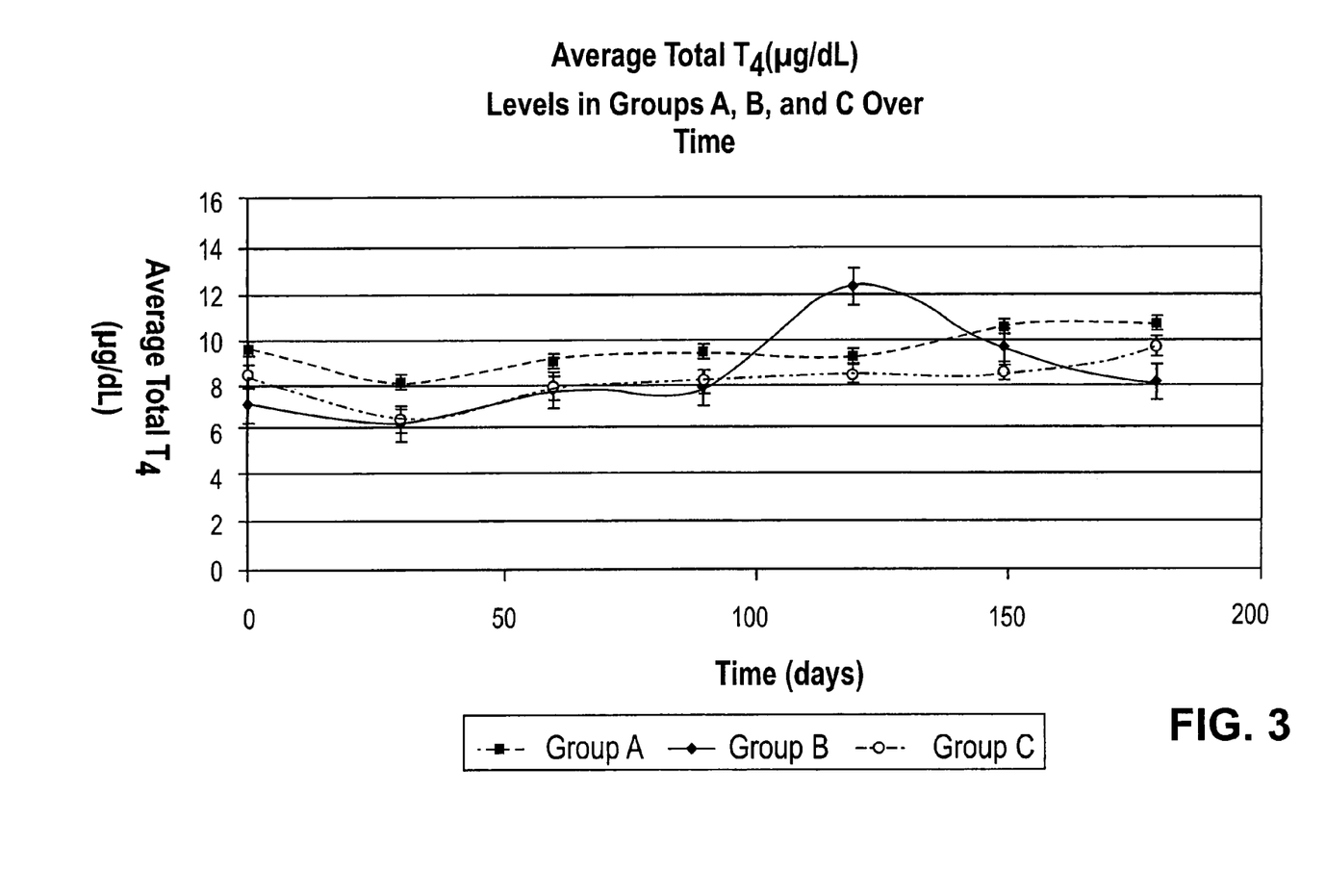
FIG. 3 illustrates T4 levels for patients in Groups A, B and C over a period of 180 days.

FIG. 3 and Table 3 illustrate T4 levels for patients in Groups A, B and C over a period of 180 days. As can be seen from FIG. 3 and Table 3, T4 levels for patients in Groups B and C as compared to group A did not significantly decrease over the 180 day period as would be expected if significant absorption of hormone had occurred.

TABLE 3

Total T4 (μg/dL) Levels in Groups A, B and C

| Group | Subject | 0 | 30 | 60 | 90 | 120 | 150 | 180 |
|---|---|---|---|---|---|---|---|---|
| A | 1 |  |  | 9.6 | 11.5 | 12.5 |  |  |
|  | 2 | 10.6 |  | 8.8 | 8.2 | 8.5 | 13.5 | 10.6 |
|  | 3 |  |  | 9.2 |  |  |  |  |
|  | 4 | 11.7 |  |  |  |  |  | 10.7 |
|  | 5 |  |  | 10.6 | 9.7 | 8.8 | 10.5 |  |
|  | 6 | 10.5 |  |  |  |  |  |  |
|  | 7 | 7.2 | 7.9 | 6.7 |  |  | 7.9 |  |
|  | 8 | 9.9 |  |  |  |  |  |  |
|  | 9 | 8.3 | 8.2 | 9.8 | 9.3 | 8.1 |  |  |
|  | 10 | 8.9 | *16.1 |  |  |  |  |  |
| B | 1 |  |  | 6.9 | 6.6 | 8.2 | 6.6 | 8.2 |
|  | 2 |  |  | 5.3 | 5.9 | 8.6 | 8.3 | 6.9 |
|  | 3 |  |  | 10.3 | 9 |  | 13.8 |  |
|  | 4 |  |  | 9.2 | 9.4 | 12 | 10.6 |  |
|  | 5 | 12.6 |  | 9.7 | 10 | 21.4 | 13.4 |  |
|  | 6 | 5.4 |  | 7 |  |  |  |  |
|  | 7 | 4.3 |  | 7 | 6.8 |  | 8 | 9.1 |
|  | 8 | 8.1 |  |  |  |  |  |  |
|  | 9 | 4.6 | 6.2 | 7 |  |  |  |  |

TABLE 3-continued

Total T4 (μg/dL) Levels in Groups A, B and C

| Group | Subject | 0 | 30 | 60 | 90 | 120 | 150 | 180 |
|---|---|---|---|---|---|---|---|---|
| C | 1 | | | 6.2 | | | | |
| | 2 | | | | | 8.4 | 12.6 | 9.5 |
| | 3 | 13.6 | | | | | | |
| | 4 | 7.1 | | | | 6.1 | 5.7 | 6.9 |
| | 5 | | | 11 | 11.8 | | | |
| | 6 | | | 6 | 6.2 | | | |
| | 7 | 9.3 | | | | | | |
| | 8 | | | | | 9.1 | | |
| | 9 | | | | | 6.6 | 10.2 | |
| | 10 | | | 6.9 | 6.5 | 7.6 | 9.8 | 9.8 |
| | 11 | 6.6 | | 6.6 | 5.6 | 7.2 | 6.8 | 9.7 |
| | 12 | | | 4.5 | 4.7 | 6.3 | 5.6 | |
| | 13 | | | 7.7 | 8.5 | 9.9 | 9.4 | |
| | 14 | | | | 7.4 | 8 | 6.6 | |
| | 15 | | | | | | | |
| | 16 | | | | | | | |
| | 17 | | | | | | | |
| | 18 | | | 8.6 | 8.5 | 9.8 | | |
| | 19 | 11.7 | | 11.7 | 12.2 | 17.2 | 14.2 | 11.9 |
| | 20 | 6 | | 7.9 | 10.2 | 10.1 | 9.3 | 10.8 |
| | 21 | 5.8 | | | | 6.9 | 6.6 | 9.6 |
| | 22 | 6.7 | | | | | | |
| | 23 | | | | | | | |
| | 24 | | 6.7 | 8.2 | 9.5 | 7.8 | 6.6 | |
| | 25 | | 6.2 | | | | | |
| | 26 | 8.5 | | | | | | |

Figure 4:
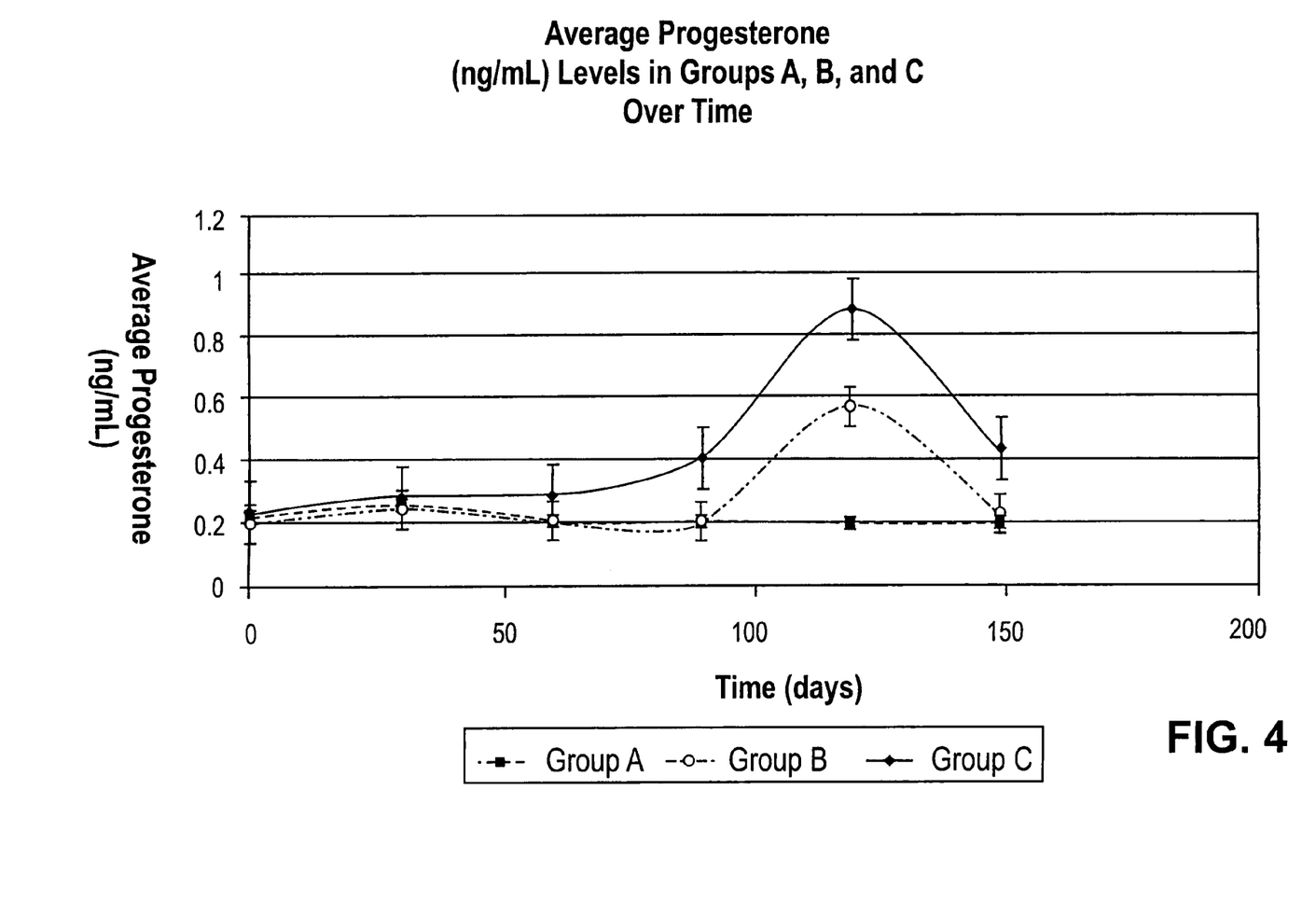
FIG. 4 illustrates progesterone levels for patients in Groups A, B and C over a period of 180 days.

FIG. 4 and Table 4 illustrate progesterone (ng/mL) levels for patients in Groups A, B and C over a period of 180 days. As can be seen from FIG. 4 and Table 4, progesterone levels for patients in Groups B and C did not significantly change. Thus, the results show no absorption of progesterone.

TABLE 4

Total Progesterone (ng/mL) Levels in Groups A, B and C

| Group | Subject | 0 | 30 | 60 | 90 | 120 | 150 | 180 |
|---|---|---|---|---|---|---|---|---|
| A | 1 | | 0.2 | 0.2 | 0.2 | 0.2 | | |
| | 2 | 0.2 | 0.4 | 0.2 | | | | |
| | 3 | 0.2 | | 0.2 | 02 | | | |
| | 4 | 0.2 | | 0.2 | 0.2 | 0.2 | 0.2 | |
| | 5 | 0.2 | | | | | | |
| | 6 | 0.2 | | | | | | |
| | 7 | 0.3 | 0.2 | 0.2 | | 0.2 | | |
| | 8 | 0.3 | | | | | | |
| | 9 | 0.2 | 0.2 | 0.2 | 0.2 | 0.2 | | |
| | 10 | 0.2 | 1.4* | | | | | |
| B | 1 | 0.2 | 0.2 | 0.2 | 0.2 | 0.2 | 0.2 | 0.2 |
| | 2 | 0.2 | 0.2 | 0.2 | 0.2 | 0.9 | 0.2 | 0.2 |
| | 3 | 0.2 | 0.2 | 0.2 | 0.2 | | 0.2 | |
| | 4 | | 0.3 | 0.2 | 0.2 | 0.3 | 0.2 | |
| | 5 | | 0.3 | 0.2 | 0.2 | 0.9 | 0.4 | |
| | 6 | 0.2 | | 0.2 | | | | |
| | 7 | 0.2 | 0.2 | 0.2 | 0.2 | | 0.2 | 0.2 |
| | 8 | | | | | | | |
| | 9 | | | | | | | |
| C | 1 | | 0.2 | 0.2 | | | | |
| | 2 | 0.2 | 0.2 | 0.2 | 0.4 | 0.2 | 0.8 | 1.2 | 0.2 |
| | 3 | | 0.2 | | | | | |
| | 4 | | 0.4 | 0.4 | | 0.3 | 0.3 | 0.3 |
| | 5 | 0.3 | | 0.2 | 0.3 | | | |
| | 6 | | 0.3 | 0.2 | 0.3 | | | |
| | 7 | 0.2 | | | | | | |
| | 8 | | 0.2 | 0.5 | 0.3 | | | |
| | 9 | 0.2 | 0.2 | 0.2 | 0.2 | 0.2 | | |
| | 10 | 0.3 | 0.3 | 0.3 | 0.3 | 0.2 | 0.6 | |
| | 11 | 0.2 | 0.2 | 0.3 | 0.2 | 0.1 | 0.2 | 0.2 |

TABLE 4-continued

Total Progesterone (ng/mL) Levels in Groups A, B and C

| Group | Subject | 0 | 30 | 60 | 90 | 120 | 150 | 180 |
|---|---|---|---|---|---|---|---|---|
| | 12 | | 0.3 | 0.2 | 0.2 | 0.2 | 0.2 | |
| | 13 | 0.2 | 0.2 | 0.2 | 0.3 | 0.2 | 0.2 | |
| | 14 | 0.2 | 0.3 | | 0.2 | 0.5 | 0.2 | |
| | 15 | | | | | | | |
| | 16 | 0.2 | | | | | | |
| | 17 | 0.2 | | | | | | |
| | 18 | 0.4 | 0.2 | 0.4 | 0.3 | 0.5 | | |
| | 19 | 0.2 | 0.4 | 0.3 | 0.5 | 1.1 | 0.3 | 0.5 |
| | 20 | | 0.6 | 0.2 | 2 | 6.3 | 0.9 | 0.2 |
| | 21 | 0.3 | | | | | | |
| | 22 | 0.2 | | | | | | |
| | 23 | 0.2 | | | | | | |
| | 24 | | 0.3 | 0.3 | 0.4 | 0.2 | 0.3 | |
| | 25 | | 0.2 | | | | | |
| | 26 | 0.2 | | | | | | |

Figure 5:
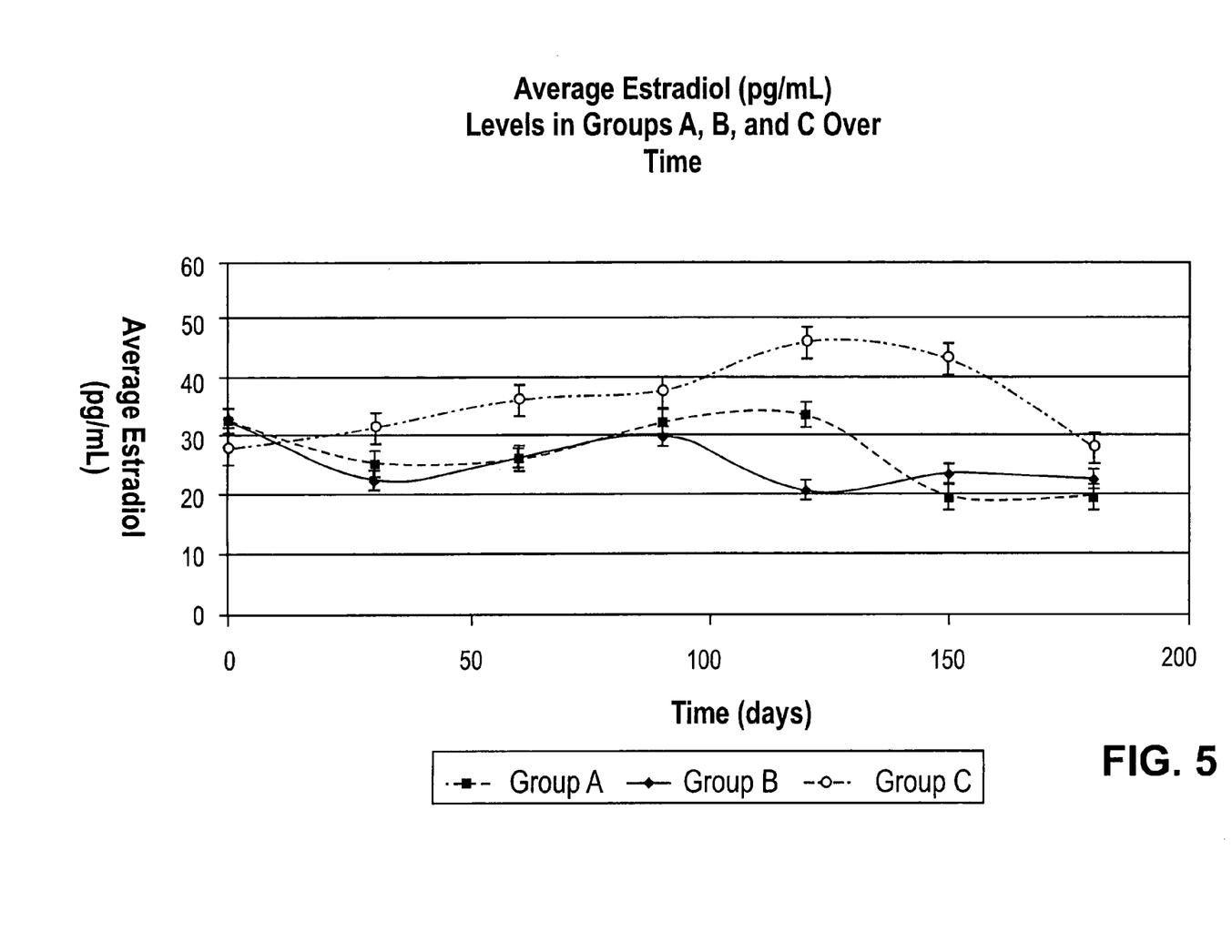
FIG. 5 illustrates estradiol levels for patients in Groups A, B and C over a period of 180 days.

FIG. 5 and Table 5 illustrate estradiol levels for patients in Groups A, B and C over a period of 180 days. As can be seen from FIG. 5 and Table 5, estradiol levels for patients in groups B and C did not change from day zero to 180 days, thus showing no clinically significant absorption of estradiol.

TABLE 5

Total Estradiol (pg/mL) Levels in Groups A, B and C

| Group | Subject | 0 | 30 | 60 | 90 | 120 | 150 | 180 |
|---|---|---|---|---|---|---|---|---|
| A | 1 | | 27 | 29 | | | | |
| | 2 | 20 | 20 | 20 | 20 | 20 | 20 | 20 |
| | 3 | 20 | | 20 | 34 | | | |
| | 4 | 49 | 40 | 48 | 56 | *195 | | |
| | 5 | 53 | | | | | | |
| | 6 | 20 | | | | | | |
| | 7 | 20 | 20 | 20 | | | 20 | |
| | 8 | 51 | | | | | | |
| | 9 | 21 | 20 | 20 | 20 | 21 | | |
| | 10 | 40 | *634 | | | | | |
| B | 1 | 20 | 20 | 20 | 20 | 28 | 24 | 20 |
| | 2 | 20 | 20 | 20 | 20 | 28 | 24 | 20 |
| | 3 | 25 | 25 | 42 | 43 | | 20.0 | |
| | 4 | | 20 | 26 | 27 | 20 | 25 | |
| | 5 | 24 | 30 | 34 | 34 | 20 | 37 | |
| | 6 | 68 | 20 | | | | | |
| | 7 | 20 | 20 | 30 | 29 | | 20 | 29 |
| | 8 | | | | | | | |
| | 9 | 54 | | 20 | | | | |
| C | 1 | | 20.0 | 20 | | | | |
| | 2 | 124 | 103 | 132 | 134 | 134 | 183 | 24 |
| | 3 | | <20 | | | | | |
| | 4 | | 29.0 | 22 | | 37 | 44 | 20.0 |
| | 5 | 20 | | 25 | 31.0 | | | |
| | 6 | 20 | 29 | 20 | 20 | | | |
| | 7 | 20 | | | | | | |
| | 8 | | 29 | 44 | 31 | | | |
| | 9 | 29 | 25.0 | 24.0 | 24.0 | 39 | | |
| | 10 | 20 | 20 | 22 | 25 | 34 | 26 | 26 |
| | 11 | 42 | 31 | 30 | 48 | 45 | 37 | |
| | 12 | 20 | 20 | 20 | 20 | 30 | 25 | |
| | 13 | 20 | 21 | 20 | 24 | 34 | 20 | |
| | 14 | 20 | 25 | | 20 | 20 | 20 | 20 |
| | 15 | | | | | | | |
| | 16 | 20 | | | | | | |
| | 17 | 20 | | | | | | |
| | 18 | 20 | 20 | 20 | 20 | 20 | | |
| | 19 | 24 | 32 | 26 | 45 | 42 | 25 | 42 |
| | 20 | | 33 | 93 | 55 | 83 | 31 | 38 |
| | 21 | 27 | | | | | | |
| | 22 | 20 | | | | | | |

TABLE 5-continued

Total Estradiol (pg/mL) Levels in Groups A, B and C

| Group | Subject | 0 | 30 | 60 | 90 | 120 | 150 | 180 |
|---|---|---|---|---|---|---|---|---|
| | 23 | 20 | | | | | | |
| | 24 | | 20 | 27 | 30 | 29 | 20 | |
| | 25 | | 47 | | | | | |
| | 26 | 20 | | | | | | |

Figure 6:
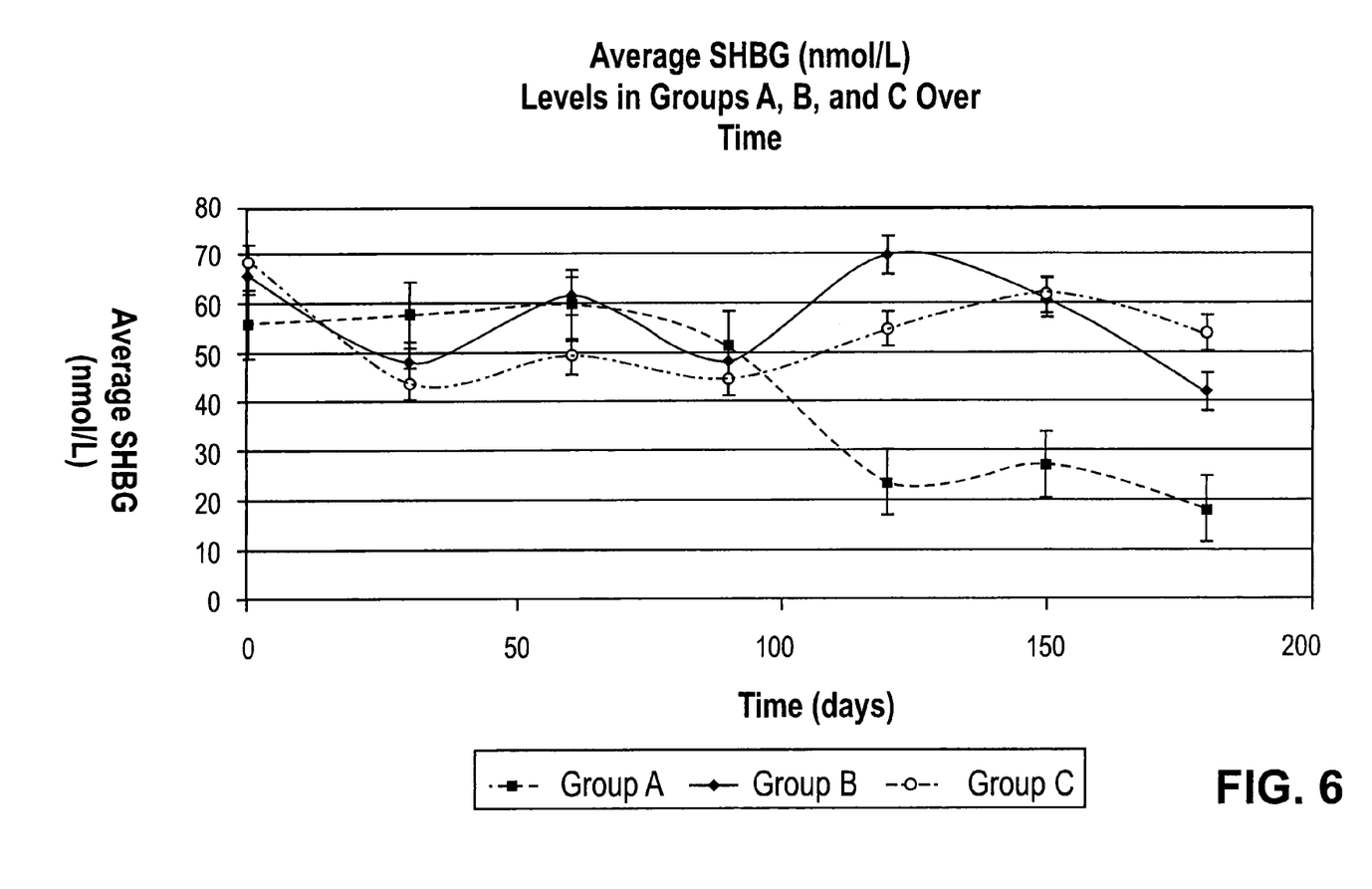
FIG. 6 illustrate SHBG levels for patients in Groups A, B and C over a period of 180 days.

FIG. 6 and Table 6 illustrate SHBG levels for patients in Groups A, B and C over a period of 180 days. As can be seen from FIG. 6 and Table 6, SHBG levels for patients in Groups B and C showed a slight insignificant decrease over the 180 day period.

TABLE 6

Total SHBG (nmol/L) Levels in Groups A, B and C.

| Group | Subject | 0 | 30 | 60 | 90 | 120 | 150 | 180 |
|---|---|---|---|---|---|---|---|---|
| A | 1 | | 65 | 58 | | | | |
| | 2 | 16 | 16 | 17 | 18 | 18 | 18 | 18 |
| | 3 | 104 | | 104 | 63 | *173 | | |
| | 4 | 139 | 135 | 62 | 77 | | | |
| | 5 | 55 | | | | | | |
| | 6 | 65 | | | | | | |
| | 7 | 32 | 37 | 30 | | | 36 | |
| | 8 | 23 | | | | | | |
| | 9 | 35 | 35 | 88 | 47 | 29 | | |
| | 10 | 33 | *80 | | | | | |
| B | 1 | 57 | 48 | 47 | 45 | 45 | 96 | 55 |
| | 2 | 57 | 57 | 45 | 52 | 66 | 70 | 42 |
| | 3 | 43 | 43 | 40 | 39 | | 57.0 | |
| | 4 | | 77 | 86 | 91 | 130 | 67 | |
| | 5 | 31 | 32 | 28 | 28 | 38 | 43 | |
| | 6 | 175 | | 148 | | | | |
| | 7 | 43 | 33 | 32 | 37 | | 32 | 29 |
| | 8 | | | | | | | |
| | 9 | 55 | | 64 | | | | |
| C | 1 | | 14.0 | 16 | | | | |
| | 2 | 170 | 187 | 140 | 158 | 124 | 180 | 163 |
| | 3 | | 40 | | | | | |
| | 4 | | 35.0 | 48 | 43 | 95 | | 62.0 |
| | 5 | 210 | | 222 | 56.0 | | | |
| | 6 | | | 21 | 23 | 26 | | |
| | 7 | 73 | | | | | | |
| | 8 | | | 18 | 17 | 20 | | |
| | 9 | 20 | 25.0 | 25.0 | 19.0 | | | |
| | 10 | 38 | 38 | 37 | 33 | 56 | 36 | 36 |
| | 11 | 12 | 10 | 10 | 10 | 11 | 15 | 12 |
| | 12 | 40 | 41 | 37 | 40 | 41 | 74 | |
| | 13 | 24 | 27 | 28 | 28 | 38 | 31 | |
| | 14 | 72 | 73 | | 63 | 95 | 109 | |
| | 15 | | | | | | | |
| | 16 | 71 | | | | | | |
| | 17 | 108 | | | | | | |
| | 18 | 41 | 35 | 38 | 36 | | | |
| | 19 | 42 | 32 | 37 | 36 | 41 | 37 | 34 |
| | 20 | | 21 | 21 | 24 | 36 | 21 | 16 |
| | 21 | 27 | | | | | | |
| | 22 | 127 | | | | | | |
| | 23 | 21 | | | | | | |
| | 24 | | 53 | 42 | 84 | 74 | 52 | |
| | 25 | | 26 | | | | | |
| | 26 | | | | | | | |

Figure 7:
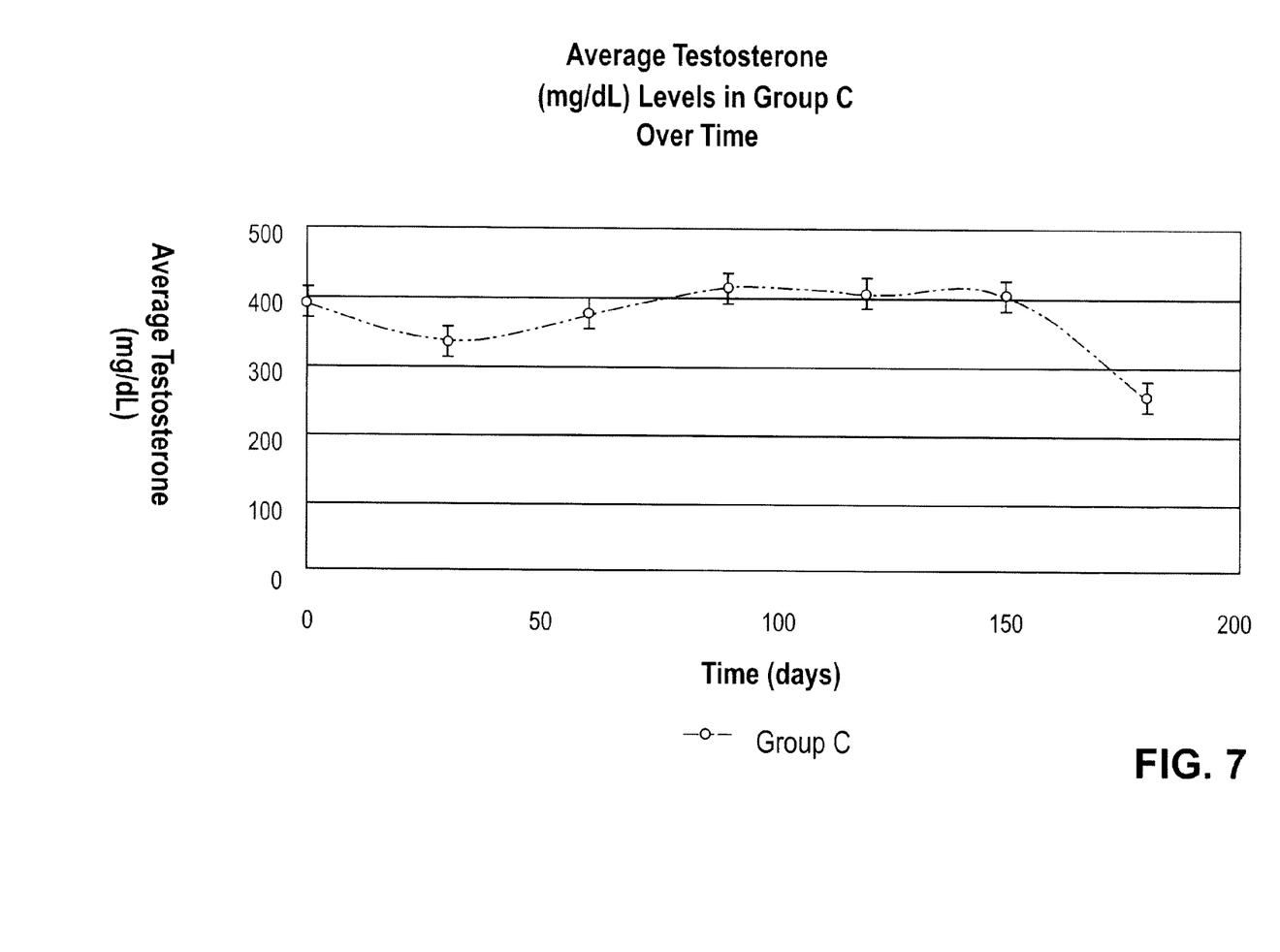
FIG. 7 illustrates testosterone levels for patients in Group C over a period of 180 days.

FIG. 7 and Table 7 illustrate testosterone levels for patients in Group C over a period of 180 days. As can be seen from FIG. 7 and Table 7, testosterone levels for patients in Group C showed no significant change over the 180 day period.

TABLE 7

Total Testosterone (mg/dL) Levels in Group C.

| Group | Subject | 0 | 30 | 60 | 90 | 120 | 150 | 180 |
|---|---|---|---|---|---|---|---|---|
| C | 1 | | 200.0 | 167 | | | | |
| | 2 | | | | | | | |
| | 3 | | 185 | | | | | |
| | 4 | | 286.0 | 422 | 311 | | | 320.0 |
| | 5 | | | | | | | |
| | 6 | | 541 | 1036 | 299 | 297 | | |
| | 7 | 574 | | | | | | |
| | 8 | | 303 | 153 | 407 | 308 | | |
| | 9 | | 206.0 | 287.0 | 226.0 | 308 | | |
| | 10 | 310 | 310 | 284 | 361 | 327 | 326 | |
| | 11 | 253 | 88 | 154 | 146 | 130 | 187 | 136 |
| | 12 | 299 | 215 | 306 | 241 | 281 | 284 | |
| | 13 | | | | | | | |
| | 14 | 754 | 845 | | 1064 | 1084 | 883 | |
| | 15 | | | | | | | |
| | 16 | | | | | | | |
| | 17 | | | | | | | |
| | 18 | 544 | 527 | 567 | 627 | 395 | | |
| | 19 | 423 | 337 | 385 | 453 | 521 | 334 | 309 |
| | 20 | | | | | | | |
| | 21 | 318 | | | | | | |
| | 22 | | | | | | | |
| | 23 | 320 | | | | | | |
| | 24 | | | | | | | |
| | 25 | 295 | 325 | | | | | |
| | 26 | 224 | | | | | | |

The above-described compositions and methods along with corresponding data provide for a convenient and safe hormone therapy with no systemic absorption or side effect.

In the preceding detailed description, specific embodiments are described. It will, however, be evident that various modifications and changes may be made thereto without departing from the broader spirit and scope of the claims. The specification and drawings are, accordingly, to be regarded in an illustrative rather than restrictive sense.

What is claimed is:

1. A method of application comprising:
    applying 0.5 ounces of a shampoo composition comprising a dihydrotestosterone blocker and a thyroid source to human skin once a day;
    rubbing the shampoo composition into the skin;
    allowing the shampoo composition to remain on the skin for a period of between five minutes and ten minutes; and
    removing the shampoo composition, wherein the amounts of the dihydrotestosterone blocker and the thyroid source are selected to treat alopecia without a clinically significant absorption of the dihydrotestosterone blocker or the thyroid source.

2. The method of claim 1, wherein the dihydrotestosterone blocker is an estrogen source.

3. The method of claim 2, wherein the estrogen source is estradiol.

4. The method of claim 1, wherein the thyroid source is a thyroid hormone.

5. The method of claim 4, wherein the thyroid hormone is triiodothyronine.

6. The method of claim 1, wherein the shampoo composition comprises approximately 100 mg of the dihydrotestosterone blocker.

7. The method of claim 1, wherein the shampoo composition comprises approximately 100 μg of the thyroid source.

8. The method of claim 1, further comprising a base suitable for application to human skin.

9. The method of claim 1, further comprising a progestagen source.

10. The method of claim 9, wherein the progestagen source is one of progesterone and synthetic progestin.

11. The method of claim 1, further comprising one of an antioxidant and a vitamin.

12. The method of claim 1, where the composition includes liposomes.

13. A method of treating alopecia comprising:
applying 0.5 ounces to one ounce of a shampoo composition comprising a dihydrotestosterone blocker and a thyroid source to human skin once a day;
rubbing the shampoo composition into the skin;
allowing the shampoo composition to remain on the skin for a period of between five minutes and ten minutes; and
removing the shampoo composition,
wherein the amounts of the dihydrotestosterone blocker and the thyroid source are selected to treat alopecia without a clinically significant absorption the dihydrotestosterone blocker or the thyroid source.

14. The method of claim 13, wherein the dihydrotestosterone blocker is an estrogen source.

15. The method of claim 13, wherein the composition further comprises a progestagen source.

16. The method of claim 13, wherein the composition further comprises one of an antioxidant and a vitamin.

17. A method of treating alopecia comprising:
applying 0.5 ounces to one ounce of a shampoo composition comprising an estrogen source and a thyroid source to human skin once a day;
rubbing the shampoo composition into the skin;
allowing the shampoo composition to remain on the skin for a period of between five minutes and ten minutes; and
removing the shampoo composition wherein the amounts of the estrogen source and the thyroid source are selected to treat alopecia without a clinically significant absorption of the estrogen source or the thyroid source.

18. The method of claim 17, wherein the composition further comprises a progestagen source.

19. The method of claim 1 wherein the dihydrotestosterone blocker is saw palmetto.

20. The method of claim 1 wherein the dihydrotestosterone blocker is an estrogen source selected from the group consisting of estradiol-17-beta, estradiol valerate, conjugated equine estrogens, piperazine estrone sulphate, estrone, estriol, estriol succinate and polyestriol phosphate.

21. The method of claim 1 wherein the thyroid source is a synthetic thyroid hormone selected from the group consisting of dessicated porcine thyroid, levothyroxine, liothyronine and liotrix.

* * * * *